United States Patent
Martinez Molina et al.

(10) Patent No.: US 11,480,578 B2
(45) Date of Patent: Oct. 25, 2022

(54) METHOD FOR IDENTIFYING A BIOMARKER INDICATIVE OF A REDUCED DRUG RESPONSE USING A THERMAL SHIFT ASSAY

(71) Applicant: Pelago Bioscience AB, Stockholm (SE)

(72) Inventors: Daniel Martinez Molina, Stockholm (SE); Par Nordlund, Stockholm (SE)

(73) Assignee: PELAGO BIOSCIENCE AB, Stockholm (SE)

( * ) Notice: Subject to any disclaimer, the term of this patent is extended or adjusted under 35 U.S.C. 154(b) by 891 days.

(21) Appl. No.: 15/127,605

(22) PCT Filed: Mar. 25, 2015

(86) PCT No.: PCT/GB2015/050895
§ 371 (c)(1),
(2) Date: Sep. 20, 2016

(87) PCT Pub. No.: WO2015/145151
PCT Pub. Date: Oct. 1, 2015

(65) Prior Publication Data
US 2018/0172697 A1    Jun. 21, 2018

(30) Foreign Application Priority Data
Mar. 25, 2014 (GB) ..................... 1405327

(51) Int. Cl.
*G01N 33/68* (2006.01)
(52) U.S. Cl.
CPC ..... *G01N 33/6842* (2013.01); *G01N 33/6803* (2013.01); *G01N 33/6848* (2013.01); *G01N 2800/52* (2013.01)

(58) Field of Classification Search
CPC .................................................. G01N 33/68
USPC .................................................. 436/86, 147
See application file for complete search history.

(56) References Cited

U.S. PATENT DOCUMENTS

| | | | | |
|---|---|---|---|---|
| 6,020,141 A | * | 2/2000 | Pantoliano | B01L 7/00 435/4 |
| 8,969,014 B2 | * | 3/2015 | Nordlund | G01N 33/6845 435/7.1 |
| 9,523,693 B2 | * | 12/2016 | Nordlund | G01N 33/6845 |
| 9,528,996 B2 | * | 12/2016 | Nordlund | G01N 33/6845 |

(Continued)

FOREIGN PATENT DOCUMENTS

| | | |
|---|---|---|
| GB | 1405327.6 | 3/2014 |
| WO | WO 1997/021833 | 12/1996 |

(Continued)

OTHER PUBLICATIONS

Ohtaka, H. et al, Protein Science 2002, 11, 1908-1916.*
(Continued)

*Primary Examiner* — Arlen Soderquist
(74) *Attorney, Agent, or Firm* — Polsinelli PC (57) ABSTRACT

The present invention concerns a method for identifying and using a biomarker, or creating a proteome profile, indicative of a reduced response to a drug in a patient involving a thermal shift assay on a sample. The method comprises the steps of a) heating a sample from a patient b) separating soluble from insoluble protein, c) analysing either or both the soluble and insoluble protein fractions of step b) to determine the melting temperature.

12 Claims, 3 Drawing Sheets

(56) References Cited

U.S. PATENT DOCUMENTS

| | | | |
|---|---|---|---|
| 2001/0003648 A1* | 6/2001 | Pantoliano | C40B 30/04 435/4 |
| 2004/0018558 A1* | 1/2004 | Gilchrist | C07K 1/047 435/7.1 |
| 2004/0106132 A1* | 6/2004 | Huang | C07K 14/47 435/6.14 |
| 2006/0019284 A1* | 1/2006 | Huang | C12Q 1/6886 435/6.14 |
| 2006/0029944 A1* | 2/2006 | Huang | C07K 14/47 435/6.14 |
| 2008/0096208 A1* | 4/2008 | Connors | C12Q 1/6886 435/6.14 |
| 2009/0304594 A1* | 12/2009 | Fantin | C12Q 1/6886 424/9.2 |
| 2012/0194522 A1* | 8/2012 | Majumdar | G06T 11/206 345/440 |
| 2014/0004530 A1* | 1/2014 | Bantscheff | G01N 33/5008 435/7.4 |
| 2014/0057368 A1* | 2/2014 | Nordlund | G01N 33/6845 436/501 |
| 2014/0142120 A1* | 5/2014 | Cardozo | A61K 31/341 514/259.2 |

FOREIGN PATENT DOCUMENTS

| | | |
|---|---|---|
| WO | WO 2007/067476 | 6/2007 |
| WO | WO 2011/050069 | 4/2011 |
| WO | WO 2012/143714 | 10/2012 |
| WO | WO 2015/145151 | 10/2015 |

OTHER PUBLICATIONS

Inglese, J. et al, Nature Chemical Biology 2007, 3, 466-479 and 17 pages of supplementary material.*
Choi, Y. L. et al, New England Journal of Medicine 2010, 363, 1734-1739 and 17 pages of supplementary material.*
Zhang, R. et al, Expert Opinion on Drug Discovery 2010, 5, 1023-1029.*
Lan, H. et al, Journal of Lipid Research 2011, 52, 646-656.*
Yap, T. A. et al, Annual Review of Pharmacology and Toxicology 2012. 52, 549-573.*
Butts, A. et al, Eukaryotic Cell 2013, 12, 278-287.*
Molina, D. M. et al, Science 2013, 341, 84-87 and 29 pages of supplementary material.*
Huang, J., New England Journal of Medicine 2013, 369, 1168-1169.*
Afanador, G. A. et al, Biochemistry 2013, 52, 9155-9166.*
Pantoliano, M. W. et al, Journal of Biomolecular Screening 2001, 6, 429-440.*
Powell, K. D. et al, Journal of the American Chemical Society 2002, 124, 10256-10257.*
Sinesterra, G. A. et al, Journal of Biomolecular Screening 2006, 11, 940-948.*
Lomenick, B. et al, Proceedings of the National Academy of Sciences of the United States of America 2009, 106, 21984-21989.*
West, G. M. et al, Analytical Chemistry 2010, 82, 5573-5581.*
Fraser, J. A. et al, Journal of Biological Chemistry 2010, 285, 37773-37786.*
Lomenick, B. et al, ACS Chemical Biology 2011, 6, 34-46.*
Arastu-Kapur, S. et al, Clinical Cancer Research 2011, 17, 2734-2744.*
Xu, Y. et al, Analytical Chemistry 2011, 83, 3555-3562.*
Suwaki, N. et al, Science Translational Medicine 201, 3, paper 85ra47, 11 pages.*
Dearmond, P. D. et al, Journal of Proteome Research 2011, 10, 4948-4958.*
Wacker, S. A. et al, HHS Public Access Author Manuscript for Nature Chemical Biology 2011, 8, 235-237.*
Minde, D. P. et al, PLOS One 2012, 7, paper e46147, 9 pages.*
Strickland, E. C. et al, Nature Protocols 2013, 8, 148-161.*
Das Thakur, M. et al, Nature 2013, 494, 251-256.*
Simon, G. M. et al, NIH Public Access Author Manuscript for Nature Chemical Biology 2013, 9, 200-205.*
Engelman, J. A. et al, Science 2007, 36, 1039-1043 and supplementary materials.*
Guix, M. et al, Journal of Clinical Investigation 2008, 2609-2619.*
Zunder, E. R. et al, Cancer Cell 14, 180-192.*
Turke, A. B. et al, Cancer Cell 17, 77-88.*
Wagle, N. et al, Journal of Clinical Oncology 2011, 29, 3085-3096.*
Ding, L. et al, Nature 2012, 481, 506-510.*
Galluzzi, L, et al, Oncogene 2012, 31, 1869-1883.*
Chan, J. N. Y. et al, Molecular & Cellular Proteomics 2012, 11, paper mcp.M111.016642, 14 pages.*
Mian, S. et al, Proteomics 2003, 3, 1725-1737.*
Nakanishi at. et al, Clinical Cancer Research 2003, 9, 3320-3328.*
Skvortsov,, S. et al, Molecular Cancer Therapeutics 2004, 3, 1551-1558.*
Loeffler-Ragg, J. et al, European Journal of Cancer 2005, 41, 2338-2346.*
Ou, K. et al, Journal of Proteome Research 2006, 5, 2194-2206.*
Dowling, P. et al, Proteomics 2006, 6, 6578-6587.*
Vergnes, B. et al, Molecular & Cellular Proteomics 2007, 6, 88-101.*
Zhang, J.-T. et al, Cancer Treatment Reviews 2007, 33, 741-756.*
Rocchetti, M. T. et al, Proteomics 2008, 8, 206-216.*
Sinisterra, G. A. et al, Journal of Biomolecular Screening 2008, 13, 337-342.*
Loeffler-Ragg, J. et al, Magazine of European Medical Oncology 2008, 1, 129-136.*
Oliveras-Ferraros, C. et al, International Journal of Oncology 2010, 37, 669-678.*
Krumbach, J. et al, European Journal of Cancer 2011, 47, 1231-1243.*
Senisterra, G. et al, Assay and Drug Development Technologies 2012, 10, 128-136.*
Yeager, M. E. et al, Proteomics Clinical Applications 2012, 6, 257-267.*
Byrum, S. D. et al, Journal of Proteomics & Bioinformatics 2013, 6, 43-50.*
Kubota, D. et al, Journal of Proteomics 2013, 91, 393-404.*
Amiri-Kordestani L, et al. (2012) Why do phase III clinical trials in oncology fail so often? J Natl Cancer Inst. 104(8): 568-569.
Bembenek ME, et al. (2011) Determination of complementary antibody pairs using protein A capture with the AlphaScreen assay format. Anal Biochem. 408(2): 321-327.
Blokzijl A, et al. (2010) Profiling protein expression and interactions: proximity ligation as a tool for personalized medicine. J Intern Med. 268(3): 232-245.
Dowling P, et al. (2006) Proteomic screening of glucose-responsive and glucose non-responsive MIN-6 beta cells reveals differential expression of proteins involved in protein folding, secretion and oxidative stress. Proteomics. 6(24): 6578-6587.
Fridlyand J, et al. (2013) Considerations for the successful co-development of targeted cancer therapies and companion diagnostics. Nat Rev Drug Discov. 12(10): 743-755.
Hanahan D, et al. (2011) Hallmarks of cancer: the next generation. Cell. 144(5): 646-674.
Jafari R, et al. (2014) The cellular thermal shift assay for evaluating drug target interactions in cells. Nature Protocols. 9: 2100-2122.
Layton CJ, et al. (2011) Quantitation of protein-protein interactions by thermal stability shift analysis. Protein Sci. 20(8): 1439-1450.
Loeffler-Ragg J, et al. (2005) Gefitinib-responsive EGFR-positive colorectal cancers have different proteome profiles from non-responsive cell lines. Eur J Cancer. 41(15): 2338-2346.
Martinez Molina D, et al. (2013) Monitoring drug target engagement in cells and tissues using the cellular thermal shift assay. Science. 341(6141): 84-87.
Niepel M, et al. (2009) Non-genetic cell-to-cell variability and the consequences for pharmacology. Curr Opin Chem Biol. 13(5-6): 556-561.

(56) References Cited

OTHER PUBLICATIONS

Niepel M, et al. (2013) Profiles of Basal and stimulated receptor signaling networks predict drug response in breast cancer lines. Sci Signal. 6(294): ra84.
Olive KP, et al. (2009) Inhibition of Hedgehog signaling enhances delivery of chemotherapy in a mouse model of pancreatic cancer. Science. 324(5933): 1457-1461.
Osmond RI, et al. (2010) Development of cell-based assays for cytokine receptor signaling, using an AlphaScreen SureFire assay format. Anal Biochem. 403(1-2): 94-101.
Savitski MM, et al. (2014) Tracking cancer drugs in living cells by thermal profiling of the proteome. Science. 346(6205): 1255784.
Solyanik GI. (2010) Multifactorial nature of tumor drug resistance. Exp Oncol. 32(3): 181-185.
Swartz MA, et al. (2012) Tumor microenvironment complexity: emerging roles in cancer therapy. Cancer Res. 72(10): 2473-2480.
Verma S, et al. (2011) In the end what matters most? A review of clinical endpoints in advanced breast cancer. Oncologist. 16(1): 25-35.
Vogelstein B, et al. (2013) Cancer genome landscapes. Science. 339(6127): 1546-1558.
Yu Z, et al. (2013) Proteomic biomarker predicts therapeutical effects of oxaliplatin combining with fluoropyrimidine in metastatic gastric cancer patients by the SELDI-proteinchip platform. Hepatogastroenterology. 60(127): 1800-1804.
Nor P, et al. (2014) Unfunded and unpublished grant application titled "Cancer biomarkers based on the cellular thermal shift assay". (8 pages).
Search Report dated Jun. 30, 2015 for GB Patent Application No. GB 1405327.6 (Applicant—Evitraproteoma AB) (5 pages).
International Search Report dated Jun. 16, 2015 for PCT/GB2015/050895 filed Mar. 25, 2015 (Applicant—Evitraproteoma AB) (5 pages).
Written Opinion dated Jun. 16, 2015 for PCT/GB2015/050895 filed Mar. 25, 2015 (Applicant—Evitraproteoma AB) (8 pages).
International Preliminary Report on Patentability dated Sep. 27, 2016 for PCT/GB2015/050895 filed Mar. 25, 2015 (Applicant—Evitraproteoma AB) (9 pages).

* cited by examiner

METHOD FOR IDENTIFYING A BIOMARKER INDICATIVE OF A REDUCED DRUG RESPONSE USING A THERMAL SHIFT ASSAY

This application is a national phase application of International Application No. PCT/GB2015/050895 filed Mar. 25, 2015, which claims priority to GB Application No. 1405327.6 filed Mar. 25, 2014, each of which is incorporated in its entirety by reference herein.

The present invention relates to methods of investigating the biochemical activation state of proteins and methods for identifying candidate biomarkers associated with reduced drug response, in particular through the use of thermal shift analysis.

More particularly, the invention relates to methods for identifying a biomarker indicative of a reduced response to a drug comprising steps of heating a sample from a patient treated with the drug and responsive to the drug and a sample from a patient treated with the drug but with a reduced response to the drug, analysing the products to determine the melting temperatures of at least one protein in each sample, and identifying at least one protein which has a different melting temperature in the sample from the drug responsive patient compared to the sample from the patient with a reduced drug response. Particularly, the at least one protein identified is other than the target protein for the drug. The method may also be used to produce a data set which represents a fingerprint for investigating drug resistance development in other patients. Further, a cell-resolved method may be carried out, where a step of cell sorting after heating the samples may be carried out, to allow analysis of a particular cell type.

Cancer is a growing global and national enigma and the growing incidence and death rates are increasing problems in many nations, including Sweden. The present annual global cancer incidence is about 12.7 million and it is estimated to be more than 20 million in 2030. Sadly, improvements in therapeutic strategies have been relatively limited. A large fraction of current cancer therapies still depend on conventional, broadly cytotoxic drugs, while more cancer specific targeted therapies have been added to the therapeutic arsenal relatively recently, with varying success. At the same time, large progress has been made by the global research community in dissecting cancer processes at the molecular, cellular and physiological level (Hanahan and Weinberg, Cell 2011 144;646). Notably, next generation sequencing technologies that allow for rapid analysis of patient cancer genomes have generated comprehensive mapping of driver mutations in different cancers and are currently being explored to understand tumor heterogeneity and drug resistance development at the genome level (Vogelstein, Science 2013 339;1546).

Based on the increasing knowledge of fundamental cancer biology, a large number of novel oncology drug targets are now being explored for the development of targeted drugs. In the right combination with other drugs, and with the use of appropriate companion biomarkers/diagnostics for therapeutic efficacy, such alternatives have raised hope for breakthroughs in cancer therapy. A few notable examples of successful targeted drugs exists, such as, for example, BRAF inhibitors in Melanoma, BCR-Abl inhibitors in Chronic Myeloid Lymphoma, as well as monoclonal antibodies directed against PD-1 (Fridlyand, Nat Rev Drug Discov 2013 12;743). However, most clinical trials of novel oncology drugs are disappointing, stressing the magnitude of the challenge (Verma, Oncologist 2011 16;25, Amiri-Kordestani, J Natl Cancer Inst 2012 104;568). Underlying reasons for this are the inherent properties of the cancer processes, the large clonal heterogeneity within tumors and between different patients, as well as the rapid evolution of drug resistance during therapy (Solyanik Exp Oncol 2010 32;181).

However, the mutational or clonal signatures of the cancer cells are only part of the story (Niepel Curr Opin Chem Biol 2009 13;556). For example, epigenetic and other cellular changes can be transferred upon cell division. Importantly, cancer cells in tumors are highly dependent on, and interacting with, the microenvironment, which is largely heterogeneous. Crosstalk with neighboring cells, including stromal cells and cells of the immune system will directly influence regulatory and metabolic processes in the cancer cell. Similarly, topography and penetration of blood vessels in the tumor will regulate the availability of oxygen and nutrients, including energy and essential metabolites, which will subsequently also affect regulatory and metabolic processes in the cancer cell (Swartz, Cancer Res 2012 72;2473). The local crosstalk and the access to oxygen and nutrients will therefore fundamentally influence the biochemical processes in the cancer cell. It is becoming increasingly clear that the states of these biochemical processes, and the extent to which the drug can modulate them, are critical determinants for the efficacy of cancer drugs. Equally important, differences in the microenvironment of the tumor and the biochemistry of the cancer cell will fundamentally change the ability of drugs to reach the anticipated target protein (Olive, Science 2009 324;1457, Niepel, Science Signaling 2013 6;294).

However, biochemical processes and drug action within the tumor environment are hard to access with current techniques. Therefore, improved strategies to generate biochemical biomarkers for monitoring drug action, including resistance development, will be critical for the development of improved cancer therapies in the future.

Surprisingly, the inventors have developed a method based on a thermal shift assay, which can be used to identify candidate biochemical biomarkers associated with drug resistance in a patient. Thus, the method can be used to identify proteins which melt at different temperatures, in samples from drug responsive and drug non-responsive patients, who have been treated with the drug. Such proteins represent candidate biochemical biomarkers, which may have different activation states in the responsive and non-responsive patient samples. Whilst thermal shift assays have been previously reported to identify the binding of a ligand (e.g. a drug) to a target protein, it was not previously realised that such assays could be used to investigate the status (e.g. the activation state) of other proteins in a sample and that such assays could therefore be used to identify biomarkers for drug resistance.

The inventors have discovered that the use of a specific thermal shift assay allows the monitoring of biochemical changes in the activation state of different proteins. Proteins have few distinct biochemical states and the inventors have shown that it is possible to differentiate between the activation states using a specific thermal shift assay. The differentiation of activation states allows the identification of proteins which have a different state in drug responsive and drug non-responsive samples. Such proteins represent candidate biomarkers for drug resistance.

The present inventors have therefore developed an assay which can be applied on the proteome level to discover novel biomarkers associated with drug resistance. Advantageously, the new method can be carried out directly on samples obtained from a patient, which allows the thermal step of the method to be performed within 3 minutes of obtaining the sample from the patient, if desired. The method can therefore allow an accurate assessment of the biochemistry of the sample and the identification of candidate biomarkers for drug non-responsiveness.

In a first aspect, the invention provides a method for identifying a biomarker indicative of a reduced response to a drug in a patient comprising the steps of
- a) heating a sample from a patient treated with the drug and responsive to the drug,
- b) separating soluble from insoluble protein in the product of step a),
- c) analysing either or both the soluble and insoluble protein fractions of step b),
- d) repeating steps a) to c) with a sample from a patient treated with the drug wherein said patient has a reduced response to the drug, and
- e) identifying at least one protein which has a different melting temperature in the sample from the drug responsive patient compared to the sample from the drug non-responsive patient, wherein said protein is a biomarker indicative of a reduced response to the drug.

The analysis step c) of the method preferably determines the melting temperature of one or more proteins. Optionally, step d) can be performed simultaneously to of before steps a) to c). When step d) is performed before or after steps a) to c), the period of time between performing the steps may be any period of time, e.g. a few minutes (e.g. between 1-10 minutes), hours (e.g. from 1, 2, 5, 10 hours), months (from 1, 2, 5, 10 months) or years (from 1, 2, 3, 4 or 5 years). The samples may therefore be obtained and treated at different times and simultaneous or directly sequential processing is not necessary (although can be done). Particularly, it will be appreciated that in the case where the samples are obtained from the same patient, e.g. from when they were drug responsive and from when they develop reduced drug responsiveness, a significant period of time may occur between collection and/or processing (e.g. heating, separation and/or analysis) of the different samples (e.g. months or years as set out above).

In another aspect, it is possible that a sample may be used in the methods of the invention from a patient who is known to be responsive to a drug, before or without drug treatment. Similarly, a sample may be used in the methods of the invention from a patient who is known to have a reduced drug response, before or without drug treatment. Although not bound by theory, it is thought that some responses to drugs may be hardwired into a cell, even in the absence of exposure to the drug itself. Thus, it may be possible to identify biomarkers for a reduced drug response merely by comparing results from patients known to be drug responsive and from patients known to have a reduced drug response. Thus, in this aspect, the present invention may provide a method for identifying a biomarker indicative of a reduced response to a drug in a patient comprising the steps of
- a) heating a sample from a patient responsive to the drug,
- b) separating soluble from insoluble protein in the product of step a),
- c) analysing either or both the soluble and insoluble protein fractions of step b),
- d) repeating steps a) to c) with a sample from a patient having a reduced response to the drug, and
- e) identifying at least one protein which has a different melting temperature in the sample from the drug responsive patient compared to the sample from the reduced drug responsive patient, wherein said protein is a biomarker indicative of a reduced response to the drug, wherein step d) is optionally carried out prior to or simultaneously to steps a) to c).

The invention further provides for a method for identifying a biomarker indicative of a reduced response to a drug in a patient comprising the steps of:
- a) heating either i) a sample from a patient having a reduced response to the drug or ii) a sample from a patient responsive to the drug;
- b) separating soluble from insoluble protein of i) or ii); and
- c) analysing either or both the soluble and insoluble fractions of step b) and either comparing with the corresponding fraction obtained from heating and separating a sample from a patient responsive to the drug when i) is heated and separated in steps a) and b), or comparing with the corresponding fraction obtained from heating and separating a sample from a patient having a reduced response to the drug when ii) is heated and separated in steps a) and b), to identify at least one protein which has a different melting temperature in the sample from the reduced drug response sample, compared to the sample from drug responsive patient.

Particularly, both samples will preferably have been exposed to the same or similar heating and separation steps e.g. heated at the same temperature (or a similar temperature e.g. within 0.5-2° C.) and/or separated by the same method.

A "corresponding" fraction refers to the same fraction in a different sample. Thus, when a soluble fraction is analysed in the reduced drug response sample, the soluble fraction is analysed in the drug responsive sample. Further, insoluble fractions are compared with each other from the different samples (drug responsive and reduced drug response).

Particularly, said patient has been treated with the drug.

Thus, as discussed above, the method of the invention is concerned with identifying a candidate biomarker for reduced response to a drug, e.g. drug resistance or non-responsiveness. The invention is based on the assessment of the status of proteins from drug responsive and drug non-responsive patient samples, where the inventors have determined that it is possible to differentiate the activation status of proteins based on their melting temperatures. Hence, in the present invention, a protein which has a different melting temperature in a sample from a drug responsive patient compared to a sample from a reduced drug response patient, e.g. a drug non-responsive patient, is likely to have a different activation status in the two samples and may represent a biomarker for drug non-responsiveness.

Proteins which have different melting temperatures in a sample from drug responsive and reduced drug responsive patients will have different solubilities at particular temperatures. Thus, when the samples are heated in step a) at a selected temperature, any proteins (biomarkers) which have a different activation state in the samples and whose melting temperatures can be distinguished at the selected temperature, will likely have different solubilities. These proteins will therefore be present in different amounts in the soluble and/or insoluble fractions from drug-responsive samples and samples from patients with a reduced drug response (e.g. drug non-responsive samples) after heating. The invention is primarily concerned with analysing samples derived from patients in order to identify proteins associated with a reduced drug response e.g. drug non-responsiveness. Such proteins (biomarkers) can be used as a future target to combat drug resistance in patients or can be used to generate a fingerprint which can identify potential drug non-responsiveness.

Whilst as indicated above, the method can be used to determine the melting temperature of at least one protein and to identify at least one protein which has a different melting temperature in the drug responsive and the reduced drug response samples, typically, the method may be used to determine the melting temperatures of a plurality of proteins and to identify any of those proteins which has a different melting temperature between the two sample types. As discussed above, whilst the melting temperature of one or more proteins can be determined in the method, this is not essential for the identification of one or more biomarkers. A difference in precipitation of a particular protein in a sample from a patient who is responsive to a drug and a sample from a patient with a reduced response to that drug is indicative that that protein may be a biomarker for a reduced response to that drug.

Typically, as set out above, more than one protein is analysed in the method and particularly at least 10, 20, 30, 40, 50, 100, 200, 500, 1000, 1500, 2000, 3000, 4000, 5000, 6000, 7000, 8000, 9000 or 10000 or more proteins may be analysed with the method of the invention. Thus, melting temperatures and/or melting curves may be established for these proteins using the method of the invention. However, this is not necessary and the method can involve simply analysing the soluble and/or insoluble fractions of the samples after heating at a selected temperature to determine whether any proteins (or a single protein) show a difference in precipitation. The method of the invention can therefore provide a proteome wide analysis of patient samples and can provide an extremely efficient way of identifying any proteins which have varying activation states between samples and which may represent candidate biomarkers for drug resistance. As discussed in further detail below, although many known analysis techniques can be used in step c), preferably when the method is used to produce melting curves for multiple numbers of proteins, mass spectrometry can be conveniently used to profile the proteins.

Preferably, the protein which is the target for the drug administered to the patient is excluded from the identification of candidate biomarkers. Thus, if a patient has become drug non-responsive, it is possible that the drug may no longer bind to the target protein. In such circumstances, the target protein may have a different melting temperature between the drug responsive and drug non-responsive samples and may be identified in the method.

Thus, a particularly preferred embodiment of the invention provides a method for identifying a biomarker indicative of a reduced response to a drug in a patient comprising the steps of
a) heating a sample from a patient treated with the drug and responsive to the drug,
b) separating soluble from insoluble protein for the product of step a),
c) analysing either or both the soluble or insoluble protein fraction of step b) by mass spectrometry to determine the melting temperature of a plurality of proteins,
d) repeating steps a) to c) with a sample from a patient treated with the drug wherein said patient has a reduced response to the drug, and
e) identifying at least one protein which has a different melting temperature in the sample from the drug responsive patient compared to the sample from the drug non-responsive patient, wherein said protein is a biomarker indicative of a reduced response to the drug.

Particularly, the method may comprise heating the respective samples at a range of different temperatures e.g. by dividing each sample into different aliquots, each to be heated at a different temperature, where determination of the melting temperature of one or more proteins is required. Further, optionally, step d) may be performed simultaneously to or before steps a) to c).

The above method may be performed on patients without or before drug treatment, i.e. on a sample from a patient responsive to the drug and on a sample from a patient with a reduced response to the drug.

As discussed above, the term "a plurality of proteins" as used herein, refers to more than one protein, typically at least 10, 20, 30, 40, 50, 100, 200, 500, 1000, 1500, 2000, 3000, 4000, 5000, 6000, 7000, 8000, 9000 or 10000 or more proteins. Although high numbers of proteins may be analysed in the present invention, the number of potential biomarkers detected may of course be much lower. The invention therefore provides for the identification of at least one biomarker (protein with a different melting temperature between the two samples). However, it is possible that the invention may identify more than 1 candidate biomarker, e.g. more than 3, 4, 5, 10, 15, 20 or 50 proteins which have different melting temperatures between the two samples (the sample from the drug responsive patient and the sample from the reduced drug response patient).

Additionally, as indicated above, the data generated from the method of the invention can be used as a fingerprint for resistance development to a particular drug. In this instance, the invention further provides a method for generating a proteome profile from a sample, indicative of a reduced response to a drug in a patient comprising the steps of
a) heating a sample from a patient treated with the drug and responsive to the drug,
b) separating soluble from insoluble protein,
c) analysing either or both the soluble and insoluble protein fractions of step b) to determine the melting temperature of a plurality of proteins,
d) repeating steps a) to c) with a sample from a patient treated with the drug wherein said patient has a reduced response to the drug, and
e) producing a proteome profile for the plurality of proteins indicating quantitative differences between the melting temperatures obtained for proteins from the sample from a patient treated with the drug and responsive to the drug and the melting temperatures obtained for proteins from the sample from a patient treated with the drug with a reduced response to the drug.

As discussed above, step d) of the methods of the invention can be performed before, after or simultaneously to steps a) to c). Further, the above method may be performed on patients without or before drug treatment, i.e. on a sample from a patient responsive to the drug and on a sample from a patient with a reduced response to the drug.

The difference or shift in the melting temperatures of a protein between the sample from a drug responsive patient and a reduced drug response patient may be at least $0.1°$ C. e.g. at least 0.2, 0.3, 0.4, $0.5°$ C. However, typically, the larger the difference or shift in melting temperatures, the more likely the protein is to be a significant biomarker for drug resistance. Thus, preferably, the difference or shift in melting temperatures is at least 1, 2, 3 or $4°$ C.

The term "sample" as used herein refers to any sample which contains a plurality of proteins. Typically, the sample is a sample obtained from a patient (e.g. a human or animal patient e.g. dog, cat, monkey, rabbit, mouse, rat etc). Preferably the patient sample used has not been subjected to a lysis step before heating step a) is carried out. Thus, preferably, the sample used in step a) contains intact cells. Particularly, the proteins to be investigated are either contained within or on the cells. The sample may be a tissue sample e.g. epithelium, muscle, nervous or connective tissue, blood, serum, plasma, lymph, cerebrospinal fluid, mucus, urine or faeces etc. Particularly, the sample may be a liquid or solid tumour sample.

The sample used in the invention may be divided into several sample aliquots for the method of the invention, which requires heating the sample at different temperatures. Hence, each sample aliquot may be heated at a different temperature. Thus, the number of individual samples used in heating step a) may depend on the number of different temperatures which it is desired to expose the sample to. In this instance, each sample aliquot is heated to only one particular temperature. Alternatively, it is possible to heat one sample and to remove an aliquot or small amount of sample after heating to each desired temperature, for analysis.

As discussed above, two types of sample are used in the present invention, namely one sample from a patient who is responsive to a drug (and preferably has been treated with that drug) and one sample from a patient who is non-responsive or has a reduced response to a drug (and preferably has been treated with the drug). Thus, the samples may be taken from drug responsive and reduced drug responsive patients, before, after, during or without drug treatment. The two samples used in the method of the invention, i.e. the drug responsive and non-responsive samples, are preferably of the same type. Thus, for example, if a tissue sample from a tumour is used as the drug responsive sample, preferably the same tissue sample type is used as the reduced drug response sample e.g. a tissue sample from a tumour. Further, preferably, the two samples are obtained from the same patient, albeit at different times. Thus, particularly, a sample may be taken from a patient at a time when they are responding to a drug treatment and a second sample may be taken from that patient when they are showing a reduced response to a drug. Further, preferably, the samples are obtained from a patient being treated under equivalent conditions e.g. the drug being administered at the time both samples are obtained is the same drug, at the same dosage, via the same route of administration, at the same time etc.

As indicated above, the patient from whom the sample is obtained maybe or is treated with a drug. Preferably, the sample which is used in the method is therefore a sample where the drug may be expected to have an effect. Therefore, if the drug is an anti-cancer therapy which is targeted to a tumour, preferably the sample used in the method of the invention would be a tumour sample.

As discussed above, the sample which may be used in the present invention may be a liquid or solid sample from a patient e.g. a tumour sample. It will be appreciated to a skilled person that such a sample may be heterogenous in nature and may comprise different cell types. It is also possible in the present invention to carry out a further step of cell resolution prior to analysis step c) of the above described method. Such a cell resolution step may allow the analysis of particular cell types in step c) which have been isolated from a heterogenous sample e.g. a tumour. In this respect, the invention provides a further step of cell sorting the samples, preferably after the heating step has been carried out. However, it is possible to carry out the step of cell sorting prior to heating the sample. If the sample is a tumour sample, a step of tumour matrix degradation may also be necessary prior to any step of cell sorting. Methods for sorting cells are well known in the art e.g. FACS. In a preferred embodiment, the present invention therefore provides a method for identifying a biomarker indicative of a reduced response to a drug in a patient comprising the steps of a) heating a sample from a patient treated with the drug and responsive to the drug, b) subjecting the product of step a) to cell sorting to isolate a cell type of interest c) separating soluble from insoluble protein in the product of step b), d) analysing either or both the soluble or insoluble protein fraction of step c) by mass spectrometry to determine the melting temperature of a plurality of proteins, e) repeating steps a) to d) with a sample from a patient treated with the drug wherein said patient has a reduced response to the drug, and f) identifying at least one protein which has a different melting temperature in the sample from the drug responsive patient compared to the sample from the reduced drug response patient, wherein said protein is a biomarker indicative of a reduced response to the drug.

Further, the invention provides a method for identifying a biomarker indicative of a reduced response to a drug in a patient comprising the steps of a) heating a sample from a patient responsive to the drug, b) subjecting the product of step a) to cell sorting to isolate a cell type of interest c) separating soluble from insoluble protein in the product of step b), d) analysing either or both the soluble or insoluble protein fraction of step c) by mass spectrometry, e) repeating steps a) to d) with a sample from a patient having a reduced response to the drug, and f) identifying at least one protein which has a different melting temperature in the sample from the drug responsive patient compared to the sample from the reduced drug response patient, wherein said protein is a biomarker indicative of a reduced response to the drug.

Optionally, step e) may be performed before or simultaneously to steps a) to d). Particularly, said patient has been treated with the drug.

The term "biomarker" as used herein refers to a protein which is present in both the drug responsive sample and the reduced drug response sample but which The term "biomarker" as used herein refers to a protein which is present in both the drug responsive sample and the reduced drug response sample but which has a different melting temperature in each of those samples. As discussed above, the difference in melting temperatures may be at least 0.1, 0.3, 0.5, 1, 1.5, 2, 2.5, 3 or 4° C. Such a biomarker may thus have a different activation state between the two sample types and may be a biomarker for drug resistance in that patient. The biomarker is not the target protein to which the drug binds to treat the patient's condition.

The term "reduced response to a drug" as used herein refers to a drug response in a patient which is not optimal compared either to results observed in other patients or compared to results which were initially obtained in that patient. Thus, a reduced response to a drug can be measured, for example, by a reduction in efficacy of the drug in terms of the amount of drug which is required to treat a patient, in terms of the length of time which is required to treat a patient or in terms of a reduction in the physical effect of the drug e.g. in tumour shrinkage. Particularly, a reduced response to a drug may be a reduction in at least 10, 20, 30, 40, 50, 60, 70, 80 or 90% of the efficacy of the drug e.g. compared to the initial response of the patient to the drug or compared to a response in another patient being successfully treated with the drug. In the methods of the invention, the drug when used to treat a patient having a reduced response to the drug in step e) may be at least 10%, 20%, 30%, 40% or 50% less efficious than the drug when used to treat a patient of step a) who is responsive to the drug. Further, a reduced response to a drug includes a patient who is non-responsive to the drug, i.e. in whom the desired effect of the drug is not seen. Thus, in this instance, the drug may not treat the condition for which it was administered. Particularly, in the case of the treatment of a cancer a patient who is non-responsive to a drug may not have any shrinkage of a tumour using that drug and may experience tumour growth.

In contrast to this, a patient who is "responsive" to a drug is one who responds to treatment with the drug, i.e. a patient in whom the drug treats the condition. Thus, a regular dosage of the drug has the physical effect desired within the time frame expected. In the treatment of cancer, a responsive patient may be one who experiences tumour shrinkage with the drug.

The term "proteome profile" as used herein is data generated from a method of the present invention which shows the differences in the melting temperatures for more than one protein in the sample. The proteome profile thus indicates at which temperatures different proteins melt in the drug responsive sample and in the drug non-responsive sample. The proteome profile may comprise melting curve information for each protein investigated, indicating the temperature range that each protein melts over in each sample.

The method of the invention may typically comprise a comparison step, where the melting temperatures of at least one protein from the drug responsive sample are compared with the melting temperature of at least one protein from the reduced drug response sample. The comparison step may result in the identification of a candidate biomarker if the melting temperatures of the protein between the samples is different.

Alternatively, where melting temperatures are not determined, the method may include a comparison step to determine any differences in solubility or precipitation between proteins which are present in the sample from the patient who is drug responsive and in the sample from the patient who has a reduced drug response. Particularly, the soluble and/or insoluble fractions of each sample after heating may be compared. Any difference in precipitation of a protein between the two samples indicates that the protein has a different melting temperature in each sample and thus potentially a different activation state.

Further, a lysis step may be carried out in the present invention. Thus, the methods of the invention may comprise a step of exposing a sample to conditions capable of causing cell lysis thereof. Preferably, any lysis step is only carried out after the heating step is carried out. Thus, more preferably, lysis is not carried out on the sample from the patient before heating is carried out. The lysis may be non-denaturing, allowing target proteins to retain a native i.e. correctly folded or native-like conformation. This is referred to herein as native lysis. This can be carried out chemically or otherwise using reagents which are well known in the art e.g. in mild buffers such as PBS or Tris at physiological pH. The degree of lysis should be sufficient to allow proteins of the cell to pass freely out of the cell. Typically, when dealing with membrane bound proteins, lysis is performed in the presence of detergents or amphiphiles, for example Triton X-100 or dodecylmaltoside, to release the protein from the membrane. The lysis step can alternatively be carried out by freeze thawing the cells or colonies. More preferably, lysis may be carried out using both native lysis buffer and freeze thawing the cells. Preferably, the lysis buffer contains lysozyme, for examples at 50-750 µg/ml, more preferably at 100-200 µg/ml. DNAse can also be found in native lysis buffer preferably at 250-750 µg/ml. Native lysis buffer may contain for example 20 mM Tris, pH 8, 100 mM NaCl, lysozyme (200 µg/ml) and DNAse I (750 µg/ml). For proteins known to be inserted into cellular membranes, detergents would be added to the lysis buffer at typical concentrations where they are known to solubilise membrane-inserted proteins in a native form, such as 1% n-dodecyl-β-maltoside. Typically, the cells will be exposed to the lysis buffer for 15-60 minutes, preferably around 30 minutes. The step of freeze thawing is preferably repeated, i.e. two or more cycles, preferably 3 or more cycles of freeze thawing are performed. In one preferred embodiment lysis is achieved by a 30 minute incubation at room temperature with lysis buffer and three×10 minutes freeze thawing.

Hence the method of the invention additionally provides a method for identifying a biomarker indicative of a reduced response to a drug in a patient comprising the steps of
   a) heating a sample from a patient responsive to the drug,
   b) exposing said sample to conditions capable of causing cell lysis,
   c) separating soluble from insoluble protein in the product of step a),
   d) analysing either or both the soluble and insoluble protein fractions of step b),
   e) repeating steps a) to d) with a sample from a patient having a reduced response to the drug, and
   identifying at least one protein which has a different melting temperature in the sample from the drug responsive patient compared to the sample from the reduced drug response patient, wherein said protein is a biomarker indicative of a reduced response to the drug. Optionally, step e) may be carried out prior to or simultaneously to steps a) to d). Particularly, said patient has been treated with the drug.

Typically, the percentage of cells lysed within a sample (e.g. a cell colony or cell culture) during the lysis step is 5-100%. Thus, it is not necessary when performing a step of lysis for all cells within a sample to be lysed.

The methods of the invention require that the sample is heated. The proteins which have a different precipitation profile at that temperature in the two samples can be identified. The temperature which is used for heating can be any temperature, as long as it is capable of causing or enhancing precipitation of one or more proteins (biomarkers) in one sample (e.g. the drug responsive sample) to a different extent than in the other sample (e.g. the reduced drug response sample).

Thus, a temperature will be capable of causing a difference in precipitation of a protein with different melting temperatures in the two samples, if the temperature selected falls between the different melting temperatures of the protein. This will allow the protein with the lower melting temperature to precipitate, whereas the protein form with the higher melting temperature will remain soluble. Further, heating at a temperature that falls within the temperature range over which a protein in a particular form (activation state) melts may provide a distinction in precipitation between protein forms with different melting temperatures. The selection of such a temperature may result in that form of the protein being present in both the soluble and insoluble protein fractions after heating at that temperature. This precipitation profile will be different to that of the protein when in a different activation state and with a different melting temperature (whether the melting temperature of that protein is higher or lower).

However, preferably, the samples are exposed to a series of different temperatures in the methods of the invention, particularly when it is desired to determine the melting temperatures of any of the proteins. Exposure to a series of different temperatures may allow the identification of more biomarkers for reduced drug response.

Therefore, in a preferred aspect, the invention provides a method for identifying a biomarker indicative of a reduced response to a drug in a patient comprising the steps of
(a) exposing a sample from a patient treated with the drug and responsive to the drug, to a series of different temperatures,
(b) separating soluble from insoluble protein in the product of step a),
(c) analysing either or both the soluble and insoluble protein fractions of step b) to determine the melting temperature of one or more proteins,
(d) repeating steps a) to c) with a sample from a patient treated with the drug wherein said patient has a reduced response to the drug, and
(e) identifying at least one protein which has a different melting temperature in the sample from the drug responsive patient compared to the sample from the drug non-responsive patient, wherein said protein is a biomarker indicative of a reduced response to the drug.

Optionally, step d) may be carried out prior to or simultaneously to steps a) to c). The above method may be performed on patients without or before drug treatment, i.e. on a sample from a patient responsive to the drug and on a sample from a patient with a reduced response to the drug.

This method of the invention requires that the sample is exposed to a series of different temperatures. This refers to a series of temperatures which may be capable of causing or enhancing precipitation of one or more proteins in the sample and typically of one or more biomarkers. Thus, in order to identify a biomarker, it is necessary for this protein to have a different melting temperature in the two samples investigated (drug responsive vs reduced drug response). This method of the invention therefore requires exposing the samples to a range of different temperatures of which at least one will cause or enhance the precipitation of at least one candidate biomarker, depending on which activation state it is in. Typically, a temperature range of 30 to 80° C. is adopted for this purpose, in order to examine at which temperatures proteins melt in one sample, compared to the other sample, i.e. in the drug responsive vs the reduced drug response sample. Thus, for example, an initial temperature of 30° C. may be selected and temperatures up to 70° C. or more may be applied to the samples (aliquots of the sample). Measurements may be taken at any interval, but typically at one degree increase, two degree increase or three degrees increase in temperature.

Some types of proteins are known to precipitate over a small temperature range. In this case, a melting curve can be generated where the initial melting temperature is the first temperature in the range and the final melting temperature is the last temperature in the range. Thus, the initial melting temperature is the lowest temperature at which a protein (e.g. a candidate biomarker) begins to precipitate e.g. at least 5% of the protein is precipitated and the final melting temperature is the first temperature at which no soluble target protein is detected. e.g. less than 5% of protein is in soluble form. Typically, at least 95% of protein is melted and precipitated.

Therefore, when a protein (e.g. a candidate biomarker) precipitates over a temperature range, the protein may begin to precipitate or unfold at a particular temperature at which point the amount of soluble protein present will begin to decrease and the amount of insoluble protein present will increase (since thermal stability is linked to solubility). Therefore, some soluble protein may still be detectable at the initial melting temperature until a slightly higher temperature is applied, at which point little or no soluble protein is detectable.

The final melting temperature for a protein is therefore a particular temperature at which there is a significant decrease of soluble protein detected, typically at least 95% of the protein is insoluble. For problematic proteins having multiple transitions, each of these transitions may result in a smaller amount of protein becoming insoluble (e.g. at least 10% of the protein becomes soluble at each transition). Where the protein precipitates over a small temperature range, where the percentage of soluble protein decreases until no soluble protein is detectable and thus the protein is completely unfolded or precipitated, an initial and final melting temperature can be determined. Hence, at the initial melting temperature of such a temperature range i.e. the lowest temperature at which target protein begins to melt or precipitate, at least 5, 10, 15, 20, 25, 30, 35, 40, 45, 50, 55, 60, 65, 70, 75, 80, 85, 90 or 95% of the protein may melt or precipitate. Alternatively viewed, at the initial melting temperature of a temperature range, the amount of soluble protein (e.g. candidate biomarker) detected decreases by at least 5, 10, 15, 20, 25, 30, 35, 40, 45, 50, 55, 60, 65, 70, 75, 80, 85, 90 or 95%. Further, the amount of insoluble target protein present may increase by at least 5, 10, 15, 20, 25, 30, 35, 40, 45, 50, 55, 60, 65, 70, 75, 80, 85, 90 or 95%.

It is also possible that a protein (candidate biomarker) may unfold and precipitate at one specific temperature. In this instance, preferably at least 95% of the protein will be in insoluble form at a specific temperature and hence the protein may not precipitate over a small temperature range. The initial melting temperature for such proteins may therefore be close to the final melting temperature.

The method of the invention as indicated above identifies proteins with different melting temperatures between drug responsive samples and reduced drug response samples. The method can detect a shift in the melting curve for a particular protein if this melts over a temperature range or a difference in the precipitation of a protein at one particular temperature.

The temperature range which can be applied in the present invention may include any temperature including the initial melting temperature at which a candidate biomarker protein begins to unfold in its most unstable activation state. Any temperature equal to or higher than the initial melting temperature will be capable of causing or enhancing precipitation of the protein. Thus, a protein with a higher thermal stability due to a different activation state (e.g. by the binding of a small molecule) will generally not unfold or precipitate at this temperature and a higher amount of soluble protein will be detected as compared to protein in the first activation state which has either completely unfolded or begun to unfold. The temperature is thus discriminatory, causing or enhancing precipitation of the candidate biomarker in its more unstable activation state to a greater extent than it causes or enhances precipitation of the protein in the more stable activation state.

The heating step can be carried out using any heat source which can heat a sample to a particular temperature. Thus, where the sample is in liquid form, then preferably the heating step may be carried out in a PCR machine. However, incubators, waterbaths etc may also be used.

As discussed above, by incubating the sample at a whole range of temperatures, it is possible to determine the temperature at which different proteins precipitate and to identify a protein which melts at different temperatures in the drug responsive vs the reduced drug response samples. Typically a temperature range may be used to produce a precipitation curve for each protein where the temperatures used are about 2, 3, 4, 5, 6, 7, 8, 9 or 10° C. different from one another. Thus the sample could be incubated at any one of more of 27, 30, 33, 36, 39, 42, 45, 48, 51, 54, 57, 60, 63, 66, 69, 72 and 75° C. as long as one of the temperatures is equal to or higher than the initial melting temperature for the protein i.e. the candidate biomarker. Where the sample is heated over a temperature range, this can be carried out in a PCR machine where an initial temperature can be set and then increased by the desired amount after a particular amount of time e.g. 0.5,1, 2, 3, 4 or 5 minutes. As discussed previously, a small aliquot or amount of sample (e.g. 1 or 2 µl) can be removed after heating at each temperature in order that the solubility of the proteins can be analysed.

Thus, the method of the invention may apply a range of temperatures to a sample from a drug responsive patient and to a sample from a reduced drug response patient. At each temperature tested, the samples are analysed to determine which proteins are soluble and/or insoluble. The results are compared (i.e. from drug responsive sample and the reduced drug response sample) to determine which proteins precipitate at different temperatures in the two samples. As discussed previously, any temperature difference may indicate that a protein is a biomarker for drug resistance or non-responsiveness. However, proteins which show large temperature differences in precipitation between the samples may be more significant biomarkers for reduced drug response in a patient.

The method of the invention further requires the use of a separation step (b) to separate soluble from insoluble proteins. The separation step can involve any separation method which is capable of separating soluble from insoluble protein. For example, a step of centrifugation can be used or a step of filtration may be used. Thus, a filter can be used to separate soluble from insoluble proteins where soluble proteins will pass through a filter. Standard filter membranes can be used for filtering heated samples where the filters will typically have a pore size from 0.015 µm to 12 µm, e.g. from 0.35 to 1.2 µm. Thus the filters may have pore sizes below 4.0 µm, or typically below 2.0 µm e.g. below 1.0 µm. It will be appreciated that filters are manufactured and marketed as having a particular pore size but the manufacturing process may occasionally result in a few smaller or larger pores; the sizes listed, which refer to the diameter, are thus the most common pore size of a given filter. Although reference is made to a range of potential pore sizes, any single filter will usually have one designated pore size e.g. 0.45 µm. Suitable filters are Super and GH polypro (from Pall) and Nucleopore (From Whatman).

It will be appreciated that proteins from different samples and from different cell types may require the use of filters with different pore sizes. Selection of a suitable filter is well within the competency of someone skilled in this field. For example, it is possible to select an appropriate pore size, by using a set of test proteins for the desired cell type or sample and investigating their behaviour with filters of varying pore sizes.

Alternatively to filtration and centrifugation, affinity capture of soluble protein can be carried out. Many antibodies and affinity reagents that recognise the folded structure of the protein will bind the soluble protein with much higher affinity than the unfolded and precipitated protein. Also the recognition of smaller tags such as poly-Histidine tags binding to metal conjugates will often correlate with solubility when these tags are less accessible in the precipitated protein. Antibodies, metal conjugates and other affinity reagents can be linked to magnetic beads or column resin which is mixed with the heat treated non-purified sample. This mix can in a subsequent step be put in an appropriate valve and washed to remove insoluble protein when this does not have high affinity to the affinity reagent. The amount of protein bound to the affinity reagent, can subsequently be measured using for example Bradford techniques, gel electrophoresis, Elisa or surface plasmon resonance detection.

It is also possible to use homogenous immune assays where the protein is detected by at least two different antibodies such as alpha-screens, elisa assays or proximity ligation assays (PLA, Blokzijl, J Intern Med 2010 268;232). When the right antibody combination has been established which specifically recognises the soluble proteins, this may give a direct signal for the amount of soluble protein present in the sample, while precipitated protein does not provide a signal. When such separation of the signal from the soluble protein and the precipitated protein can be directly accomplished in a homogenous assay, no physical separation of the soluble and precipitated protein is required to measure melting curves for this specific protein. Thus, when the method of detection involves the use of two different antibodies, the separation step b) may be excluded. In this instance the invention provides a method for identifying a biomarker indicative of a reduced response to a drug in a patient comprising the steps of a) heating a sample from a patient treated with the drug and responsive to the drug,
b) analysing the product of step a) using at least two antibodies,
c) repeating steps a) and b) with a sample from a patient treated with the drug wherein said patient has a reduced response to the drug, and
d) identifying at least one protein which has a different melting temperature in the sample from the drug responsive patient compared to the sample from the drug non-responsive patient, wherein said protein is a biomarker indicative of a reduced response to the drug.

Optionally, step c) may be performed prior to or simultaneously to steps a) and b). The above method may be performed on patients without or before drug treatment, i.e. on a sample from a patient responsive to the drug and on a sample from a patient with a reduced response to the drug.

It will be appreciated that in this aspect of the invention other affinity reagents may be capable of detecting soluble protein in a sample in a similar way to the two antibodies described above. In this aspect, again the method may not employ a separation step as the analysis step involves detection of a soluble (or native protein) using two or more affinity reagents which bind with a higher affinity to the soluble or native form of the protein than to the unfolded or insoluble (precipitated) form of the protein.

In this way, such affinity reagents can determine whether soluble or native forms of the protein are present in a sample after heating and thus any difference in precipitation of a protein between drug-responsive and drug non-responsive samples can be detected. The two or more affinity reagents must together be capable of distinguishing between soluble or native, and unfolded and/or insoluble forms of a protein and thus must be capable of detecting soluble or native protein against a background of other proteins (both soluble and insoluble) and any insoluble protein that may also be present.

This form of the method of the invention is particularly advantageous as there is no specific requirement to carry out a separation step and particularly no separation step may be carried out. In this respect, the method of this embodiment involves minimal processing steps, which potentially allows automation of the method and an increased throughput, where large numbers of samples can be handled.

The "affinity reagent" as used herein thus refers to any reagent which is capable of binding with a higher affinity to a soluble or native form of a protein than to an unfolded and/or insoluble form of the same protein. An affinity reagent which binds with a higher affinity to a soluble or native form of a protein compared to the unfolded and/or insoluble form of the protein will have a smaller $K_D$ value for its association with the soluble or native target protein than for its association with the unfolded and/or insoluble form of the protein. Particularly, an affinity reagent of the present application may have a $K_D$ value which is at least 100 times smaller with respect to binding to the soluble or native form of the protein than the $K_D$ with respect to binding to the unfolded and/or insoluble form of the protein. Methods for measuring the $K_D$ values of affinity reagents are well known in the art. Thus, the use of two or more affinity reagents (e.g. antibodies) for the detection of the soluble or native protein allows the use of affinity reagents which may have a lower specificity for the soluble or native protein than if a single affinity reagent (e.g. antibody) was used alone to detect the soluble or native protein. As two or more affinity reagents (e.g. antibodies) are required to be bound to the soluble or native protein to result in its detection, less specific affinity reagents can be used and can still result in a specific method of detecting the soluble or native protein. Thus some binding of at least one of the affinity reagents (e.g. antibodies) may occur to the unfolded and/or insoluble form of the protein, although binding to the soluble or native form of the protein is preferential and association may be at least 100 times greater than association to the unfolded and/or insoluble form of the protein. Similarly, each affinity reagent particularly binds with higher affinity to the soluble or native form of the protein than to any other protein present in the sample.

In a particular embodiment, at least one of the affinity reagents (e.g. antibodies) used the method is capable of binding specifically to the soluble or native form of the protein but not to the unfolded and/or insoluble form of the protein (or to any other protein). Thus, the reagent may bind specifically to the soluble or native protein and any binding to the unfolded and/or insoluble protein may be non-specific and minimal. Thus, in this instance, one affinity reagent is capable of specific binding and one or more other affinity reagents may be capable of binding to the soluble or native form of the protein with higher affinity than to the unfolded and/or insoluble form of the protein. Further, the method provides for the use of two or more affinity reagents which bind specifically to the soluble or native form of the protein but not to the unfolded and/or insoluble form of the protein.

In order to distinguish soluble (or native) from unfolded and/or insoluble protein, the affinity reagent may recognize (particularly specifically recognize) an epitope or sequence of the protein which is exposed in the soluble or native form of the protein but not in the unfolded and/or insoluble form of the protein. The two or more affinity reagents recognise different epitopes or sequences on the protein and thus provide a more specific method of distinguishing soluble or native from unfolded and/or insoluble protein, than when identifying a single epitope or sequence. (Although with proteins which are homodimers, the affinity reagents may be directed to the same epitope). Thus, both (or more) affinity reagents must be bound to the protein in order to determine that a soluble or native form of the protein is present. A positive detection of soluble or native protein is only achieved if both (or more) affinity reagents (e.g. antibodies) are bound.

The affinity reagent may be an antibody, antibody fragment, affibody, peptide, aptamer, DARTs or other small molecule that binds to the soluble or native form of a protein with a higher affinity than to the unfolded and/or insoluble form of the protein. Particularly, at least one affinity reagent is an antibody and more particularly two antibodies are used per protein to be detected in the method. The invention however also encompasses the use of different affinity reagents e.g. the use of an antibody and another affinity reagent. Since more than one protein may be analysed in each sample (i.e. in each drug responsive and drug non-responsive sample), multiple affinity reagents may be used in each analysis step, where at least 2 affinity reagents are used for each protein to be detected. Where multiple proteins are to be analysed, the signals generated by the binding of the two or more affinity reagents to each protein should be different.

The detection of the two or more affinity reagents (particularly two antibodies) may be using a reporter assay which results in a signal change when the two or more affinity reagents are bound to soluble or native protein. Generally, the two or more affinity reagents are labeled (particularly with different labels) and the close proximity of those labels to one another when bound via the affinity reagents to the soluble or native form of the target protein results in a change in signal e.g. the emission of fluorescence or the production of light or fluorescence at a different wavelength (to the labels when used alone) or the quenching of fluorescence. Such reporter assays are often referred to as proximity reporter assays, e.g. a FRET (fluorescence resonance energy transfer) based method (or a variant thereof, such as BRET (Bioluminescence Resonance Energy Transfer)) may be used in the present method for detection, where the close association of one label (a donor molecule) attached to an affinity reagent, to a second label (an acceptor molecule) attached to an affinity reagent, results in the production or alteration of a signal. Thus, the presence of the two or more labels bound to the soluble or native protein via the affinity reagents results in a detectable signal change. In one embodiment e.g. FRET, transfer of energy from the donor to the acceptor molecule labels may result in the emission of fluorescence by the acceptor molecule. In this way, the labeling of two (or more) affinity reagents (antibodies) which bind to the soluble form of a protein, with labels which have a signal change when in close proximity to each other, can result in the emission of fluorescence when both are bound to the soluble protein, thus enabling detection of the soluble target protein. Donor and acceptor molecules used in FRET/BRET based methods are well known in the art and include pairs such as cyan fluorescent protein and yellow fluorescent protein (both variants of green fluorescent protein); and bioluminescent luciferase and YFP. Such a method requires the binding of both (or more) affinity reagents (e.g. antibodies) to the soluble protein before detection of any signal (e.g. luminescence) is achieved. In this aspect, one affinity reagent may be labeled with donor molecule and the second affinity reagent may be labeled with the acceptor molecule.

In a particular embodiment, the labels which demonstrate a signal change when in close proximity (e.g. when bound via affinity reagents to the soluble protein),e.g. donor and acceptor molecules, may be coated or comprised within separate bead populations which may then be used to bind to each affinity reagent (antibody). Thus, the beads coated with one of the labels (e.g. the donor molecule) may be used attached to the first affinity reagent e.g. antibody and the beads coated with the second label (e.g. the acceptor molecule) may be used to detect the second affinity reagent (e.g. antibody). Each bead population (e.g. donor or acceptor) may be conjugated with a further reagent to allow binding to either the first or second affinity reagent (e.g. antibodies). For example, a bead population (donor or acceptor) may be streptavidin coated to allow binding to biotinylated affinity reagent (e.g. antibody) or maybe conjugated to protein A to allow binding to an antibody affinity reagent. Methods of attaching beads to affinity reagents such as antibodies are well known in the art.

It will be appreciated that the two or more affinity reagents (e.g. antibodies) may be labeled (e.g. with donor or acceptor molecules) prior to addition to the sample or after addition to the sample. However, particularly, the affinity reagents (antibodies) may be labeled before addition to the sample. The AlphaScreen Surefire assay format (Perkin Elmer) may be particularly used in the method of the invention, where other antibodies may be attached to the beads provided (see Osmond et al, Analytical biochemistry, 403, 94-9101, 2010, incorporated herein by reference).

Other methods for detection of the bound affinity reagents include proximity ligation assays (such as Duolink from Olink) and ELISAs.

Methods for producing affinity reagents, such as antibodies which may bind to the soluble form of a protein but not the insoluble form of a protein are known in the art. For example, the study of the 3D structure of a soluble and insoluble protein can enable determination of epitopes which are exposed on the soluble form but not the insoluble form. Antibodies or peptides which bind to such epitopes can then be produced using standard methods.

Further, methods are known which can be used to identify antibody pairs that bind to a protein e.g. methods employing surface plasmon resonance biosensors or ELISA. Further, Bembenek et al (Analytical Biochemistry, 408, 2011, 321-327, incorporated herein by reference), reported a bead based screening method using antibody capture on Protein A Alphascreen beads to analyse and select pairs of antibodies capable of binding to the same target.

In this aspect, the invention additionally provides a method for determining whether a protein is a biomarker indicative of a reduced response to a drug in a patient comprising the steps of
  a) heating a sample from a patient responsive to the drug,
  b) analysing the product of step a) for the presence of the soluble form of said protein using at least two affinity reagents which are capable of binding to the soluble protein with a higher affinity than to an unfolded or insoluble form of the protein,
  c) repeating steps a) and b) with a sample from a patient having a reduced response to the drug, and
  d) determining whether there is any difference in the amount of soluble protein present in the drug responsive and reduced drug response samples,
    wherein if a difference is detected, the protein is a biomarker indicative of a reduced response to a drug.

Particularly, said patient has been treated with the drug.

In this aspect, the sample may be particularly heated to a temperature which is capable of causing precipitation of the protein in one activation state to a greater extent than it is capable of causing precipitation of the protein in a different activation state. Particularly, the sample may be heated at a temperature which falls either within the temperature range over which the protein melts (i.e. in either form or activation state) or between the different melting temperatures of the protein when in the different activation states in the drug responsive and reduced drug response samples.

Alternatively viewed, the invention provides a method for identifying a biomarker indicative of a reduced response to a drug in a patient comprising the steps of:
  a) heating a sample from a patient responsive to the drug,
  b) analyzing the product of step a) using at least two affinity reagents which are capable of binding to a soluble protein with a higher affinity than to an unfolded or insoluble form of the protein,
  c) repeating steps a) and b) with a sample from a patient having a reduced response to the drug and
  d) identifying at least one protein which has a different melting temperature in the sample from the drug responsive patient compared to the sample form the drug non-responsive patient, wherein said protein is a biomarker indicative of a reduced response.

Particularly, in this aspect, said at least one protein which has a different melting temperature in the drug responsive and reduced drug response samples is identified by detecting a difference in the amount of a soluble form of a protein present in the two samples. Optionally step c) can be performed prior to or simultaneously to steps a) and b).

Particularly, said patient has been treated with the drug.

According to the methods of the invention it is possible to analyse either (or both) the insoluble or soluble fractions for the presence of target protein. However, if the analysis step requires the use of affinity reagents which are capable of binding to a soluble protein with a higher affinity than to an unfolded or insoluble form of the protein, then either the soluble fraction is analysed (where a separation step is also employed) or the whole sample is analysed (if no separation step is employed). In methods where the insoluble fraction is to be analysed, this fraction is preferably solubilised prior to analysis, for example, the precipitated proteins may be dissolved in loading buffer prior to application to separation gels. Preferably the methods of the invention involve a step (c) (or step d) when a cell sorting step is carried out) of analysing the protein fraction(s). The methods of the invention thus particularly comprise an analysis step. Thus, the soluble proteins obtained after the step of separation (or after heating if no separation is carried out) are preferably analysed for the presence of protein. Hence, if a centrifugation separation step was carried out, the supernatant can be analysed for the presence of target protein and where a filtration separation step was carried out, the proteins which pass through the filter i.e. the filtrate can be analysed for the presence of protein.

The proteins can be detected by various different methods. Detection may be based on affinity binding between a protein and a detection moiety, for example an antibody, antibody fragment or affibody (non Ab based protein binding partner). Preferably, proteins may be detected using antibodies, monoclonal or polyclonal, directed to the protein. When the method is used to investigate a plurality of proteins, analysis of the proteins may be carried out using an antibody array. Such methods allow for rapid and reliable analysis of a wide variety of proteins. Protein affinity arrays, based on specific antibodies can be used to quantify protein. For example a Kinase Antibody are featuring specific monoclonal antibodies to 276 different human protein kinases can be used (Full Moon Biosystems).

However, in a preferred embodiment of the invention, the soluble fraction from step b) or the solubilised insoluble fraction from step b) may be analysed with mass spectrometry e.g. using semi quantitative or preferably quantitative mass spectrometry (MS). In a fourier transform ion cyclotron resonance experiment using an orbitrap instrument typically 1000-10 000 proteins can be detected simultaneously in a sample from a lysate. Preferably and LC-MS analysis will be run using a isobaric labeling strategy such as ITRAQ but preferably with TMT10 (Thermo-Fisher Scientific) allowing 10 temperatures to be measured and normalized for each sample in the same experiment. The MS measurement would be done on an instrument such as a Orbitrap Q Executive or Fusion (Thermo-Fisher Scientific). Measurement for the 10 temperatures for each protein can subsequently be used to describe the characteristic melting curve. In a preferred embodiment a temperature scan of cells followed by lysis, filtration and in a final step the detection of all remaining soluble protein using mass spectrometry, at each temperature of the scan, allows precipitation curves to be measured in parallel for many proteins. This global proteome melting curve analysis allows for the identification of proteins which have different melting temperatures between the patient samples examined in the present invention. The global proteome melting curve analysis for thermal shift changes allow this to be performed for the proteins which are available at sufficient level to be detectable with MS.

The analysis step of the methods of the invention therefore generally requires the detection of at least one protein in either the soluble or insoluble fractions, or in the sample if no step of separation is carried out. The step of identifying at least one protein that has a different melting temperature in the sample from the drug responsive patient compared to the sample from the reduced drug response patient involves comparing the soluble fractions from each sample to determine whether a protein (or multiple proteins) is present in different amounts. Alternatively, or additionally, the insoluble fractions from each sample after heating can be compared to determine whether a protein (or multiple proteins) is present in different amounts. Particularly, if the sample is heated at a temperature which falls between the melting temperatures of a protein in different activation states, a protein may be present only in the soluble or insoluble fractions in a drug responsive sample but not present in the corresponding fraction in a reduced drug response sample, or vice versa.

The detection of a "different amount" of protein may relate to the actual amount of a protein which is present which is present, but more particularly may relate to the relative amount of a protein that is present. The relative amount of a protein may be determined by comparing the amounts of that protein in the soluble and insoluble fractions of the same sample (e.g. as a percentage, ratio or fraction). Thus, if a protein is only present in the soluble fraction of a sample, then the relative amount of protein present in that fraction can be indicated as 100%. If the relative amounts of a protein in a particular fraction differ between samples, then the protein is likely to be a biomarker. An amount of protein may differ by at least 5, 10, 15, 20, 30, 40, 50, 60, 70, 80, or 90%.

The methods of the present invention may be used to identify biomarkers for drug resistance, as discussed above. Thus, biomarkers identified by the method of the invention may be used to guide cancer therapy. It is possible to investigate the drug therapy by repeated investigations of tumour samples before and throughout therapy. Hence, clinical samples from resistant and metastatic cancers can be analysed and compared to initial samples to establish the extent and the mechanism for drug resistance at the biochemical level. Further, fresh tumour samples can serve as analogs for the cancer locus in vivo. Treatment of fresh tumour samples with different drugs and monitoring of initial biochemical responses using the identified biomarkers has the potential to provide critical information for how a cancer will respond at the biochemical level to a set of drugs.

The methods of the invention will also be useful to address efficacy and resistance development during combination therapy. Complex biochemical changes due to resistance will be possible to determine using biomarkers identified by the invention methods.

In another aspect, the invention also provides a method of determining drug responsiveness in a patient comprising:
(a) heating a sample from a patient treated with said drug
(b) separating soluble from insoluble protein in the product of step a) and
c) analysing either or both the soluble and insoluble protein fractions of step b) for the presence of a target protein.

In this method, the target protein maybe any protein which is indicative of drug responsiveness e.g. a biomarker. Particularly, the target protein may have a different activation state in drug responsive vs reduced drug responsive patients. Identification of a particular activation state of a protein in a sample can therefore be indicative of drug responsiveness in a patient.

Therefore, alternatively viewed, the invention provides a method of determining the activation state of a protein in a sample comprising:
(a) heating a sample
(b) separating soluble from insoluble protein in the product of step a) and
c) analysing either or both the soluble and insoluble protein fractions of step b) for the presence of the protein.

As described above, the activation state of a protein in a sample e.g. a patient sample can be determined by heating the sample at a temperature which produces a difference in precipitation between the activation states of a protein. Thus by heating a sample for a particular protein, the activation state of that protein can be determined by investigating the amount of protein which is precipitated.

In a further embodiment, the method can also be used to determine whether a recombinantly produced drug or a newly developed drug has the same or similar structure to an approved drug or to another reference drug. In this instance, the method of the invention can be used to determine whether a drug still binds to its target and a melting curve can be generated for the protein for comparison with both the approved (or reference) and the recombinantly produced drug. Alternatively, for protein drugs, the method can be used to determine directly whether a recombinantly produced protein drug has a similar or same structure as an approved drug (or reference drug). In this instance, a melting curve can be produced for both the recombinantly produced drug and the approved drug (or reference drug) and these can be compared. A recombinantly produced drug with a similar or the same melting curve as an approved drug is likely to have a similar structure. The recombinantly produced drug and approved drug (or reference drug) can also be heated at a single temperature and the difference in precipitation at that temperature can be compared to determine whether the structures are similar. Thus, a method for investigating the structural identity between a recombinantly produced drug and an approved drug (or reference drug) is encompassed, comprising the steps of:

a) heating a sample comprising a recombinantly produced drug, b) analysing the product of step b)

c) repeating steps a) and b) with a sample comprising an approved drug or reference drug, d) identifying any difference in the melting temperature of the recombinantly produced drug and the approved drug or reference drug, wherein a difference in melting temperatures is indicative of a difference in structures. Optionally, step c) may be carried out before or simultaneously to steps a) and b)

In the above method, a recombinantly produced drug can be produced by any known recombinant method of the art e.g. expression in a bacterial cell. An approved drug is one for which marketing approval has been granted in a country. A reference drug is any drug to which it is desired to compare the structure of the recombinantly produced drug with. As indicated above, the above method may preferably involve heating the samples at a range of temperatures to determine any difference in the melting curves.

The invention will now be further described in the following non-limiting Examples in which:

FIG. 2—Thermal shift assay showing the identification of the biochemical states of biomarkers. A) p53 with two cognate duplex oligos (PG1, and PG2) added to lysed A549 cells containing wild type p53, b) Ribonucleotide reductase R2 in a metal depleted form and with the natural cofactor iron, c) protein kinase A, response to cAMP treatment by the regulatory (Reg) and catalytic domains.

EXAMPLE 1

Materials and Methods

Human cancer cell line A549 (ATTC no. CCL-185) was cultured in RPMI-1640 medium (Sigma-Aldrich) containing 0.3 g/L L-glutamine and supplemented with 10% fetal bovine serum (FBS, Gibco/Life Technologies, Carlsbad, Calif., USA), 100 units/mL penicillin and 100 units/mL streptomycin (Gibco/Life Technologies) to short-term passages (3-15) in an incubator chamber (with 5% $CO_2$).

Lysates of the cells were prepared by harvest of cells and suspending cell-pellet in Phosphate-buffered saline (PBS) to a cell concentration of 100000 cells/ml, freeze-thawed three cycles in $N_2$ (I) and the lysed cells were cleared from cell debris by centrifugation. The cleared lysate was divided in three equal parts, and supplemented with DNA oligos PG1 or PG2 dissolved in ultrapure water, and as a control an equal amount of water was added to the third aliquot.

Figure 1:
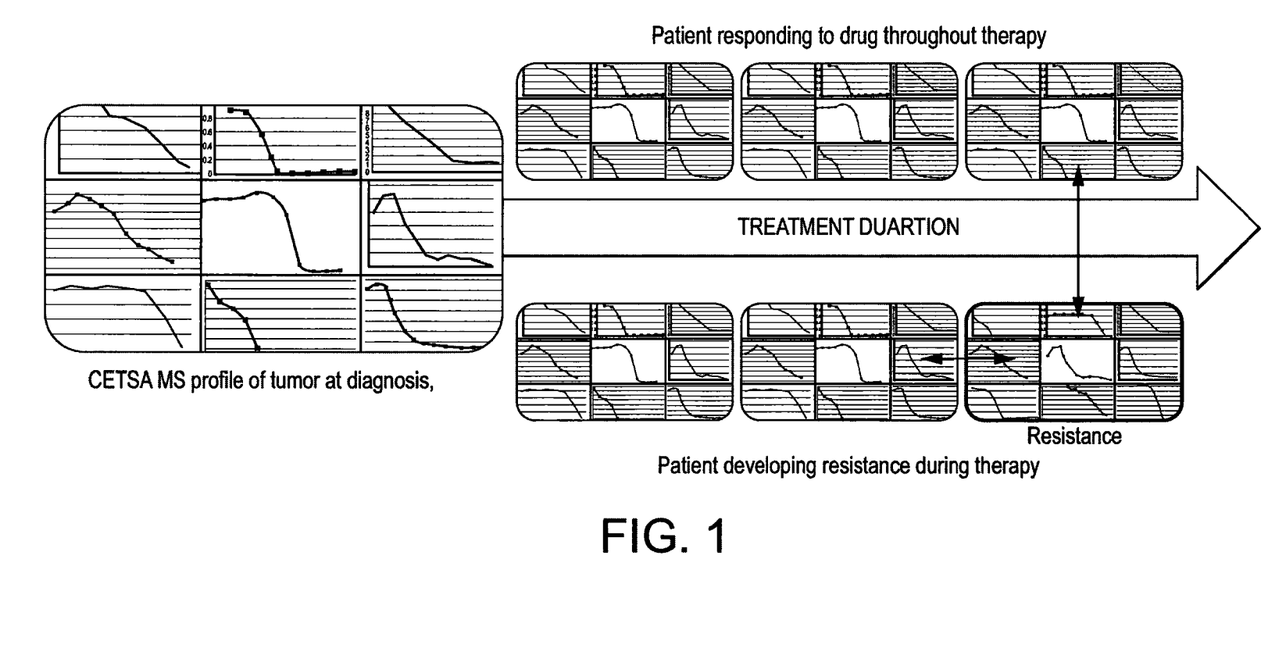
FIG. 1—A schematic view of the invention applied to generate biomarkers for drug resistance development. Biomarkers for resistance development show significant differences in melt curves between resistant and non-resistant patient samples (exemplified by arrows)
Figure 2A:
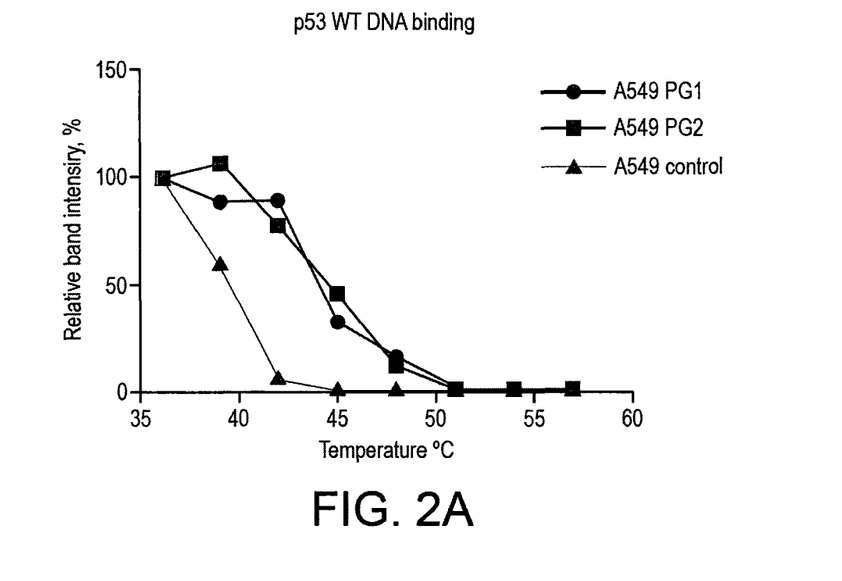

Following incubation for 30 minutes at room temperature, the three samples were aliquoted to 8 tube PCR strips and heated to increasing temperatures (36 to 57° C. with three degree increments) for duration of three minutes. After heating the samples were cooled and precipitated protein was separated by centrifugation at 20000*g for 17 minutes. The remaining supernatants, containing various amounts of soluble protein was subjected to standard SDS-Page and Western blot analysis using a specific primary p53 antibody (Santa Cruz Biotechnology SC-126) at 1:400 dilution in non-fat dietary milk. The resulting protein bands on the Western blot membranes were integrated and plotted using Graphpad Prism 6.0 software. The results for the thermal shift assay can be seen in FIG. 2a

EXAMPLE 2

Materials and Methods

Figure 2B:
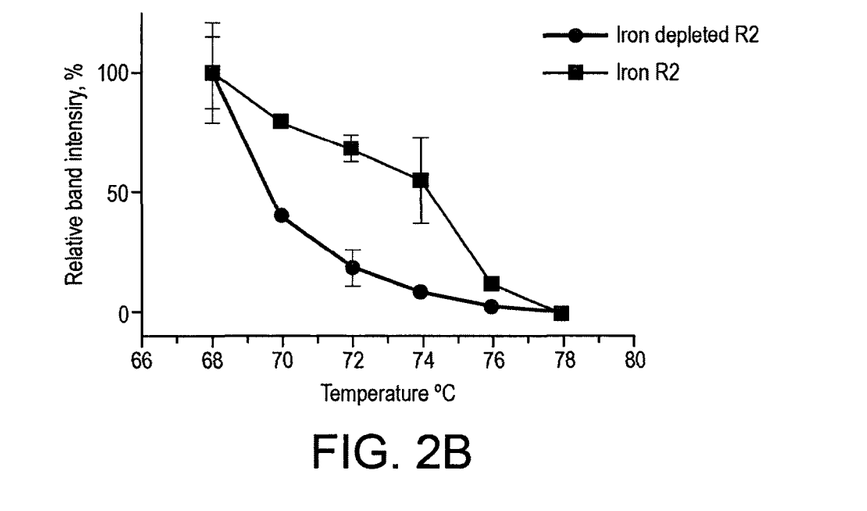

Cells were grown and lysed as described in Example 1. After clarification of the lysate, the supernatant was divided into equal parts, one supplemented with a final concentration of 5 mM EDTA to chelate out metal ions. The control sample was supplemented with an equal amount of ultrapure water. After incubation for 10 minutes at room temperature, the lysates were aliquoted into 8 tube PCR strips and heated to increasing temperature (68 to 78° C. with two degree increments) for duration of three minutes. After heating the samples were cooled and precipitated protein was separated by centrifugation at 20000*g for 17 minutes. The remaining supernatants, containing various amounts of soluble protein was subjected to standard SDS-Page and Western blot analysis using a specific primary RNR R2 antibody (Santa Cruz Biotechnology SC-10846) at 1:400 dilution in non-fat dietary milk. The resulting protein bands on the Western blot membranes were integrated and plotted using Graphpad Prism 6.0 software. The results for the thermal shift assay can be seen in FIG. 2b.

EXAMPLE 3

Materials and Methods

Figure 2C:
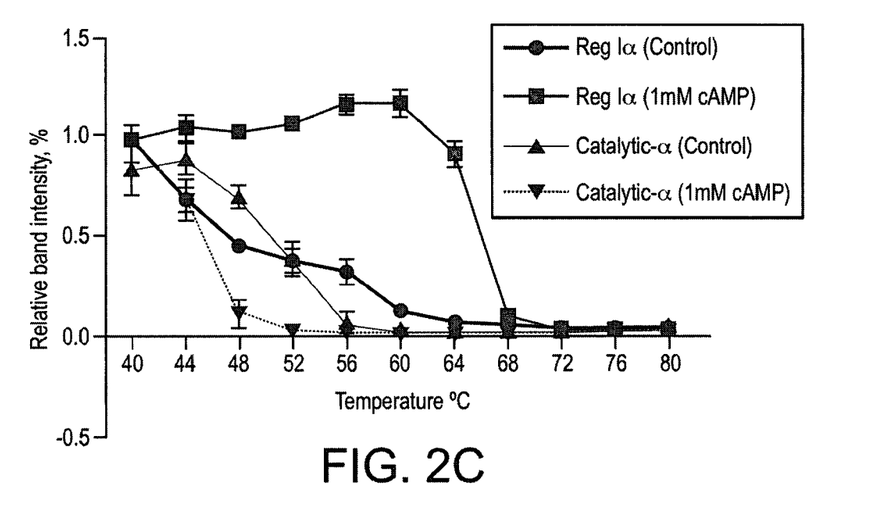

Cells were grown and lysed as described in Example 1. After clarification of the lysate, the supernatant was divided into equal parts, one supplemented with a final concentration of 1 mM cyclic AMP dissolved in ultrapure water. The control sample was supplemented with an equal amount of ultrapure water. After incubation for 10 minutes at room temperature, the lysates were aliquoted into 8 tube PCR strips and heated to increasing temperature (40 to 80° C. with four degree increments) for duration of three minutes. After heating the samples were cooled and precipitated protein was separated by centrifugation at 20000*g for 17 minutes. The remaining supernatants, containing various amounts of soluble protein was subjected to standard SDS-Page and Western blot analysis using a specific primary Protein Kinase A antibodies against catalytic subunit alpha and regulatory subunit 1 alpha (Santa Cruz Biotechnology SC-48412 and SC-136231, respectively) at 1:400 dilution in non-fat dietary milk. The resulting protein bands on the Western blot membranes were integrated and plotted using Graphpad Prism 6.0 software. The thermal shift assay results can be seen in FIG. 2c.

EXAMPLE 4

Materials and Methods

Human cancer cell line K562 and mouse fibrosarcoma cell line T241 with endogenous expression of GFP, were cultured to short-term passages (3-15) in an incubator chamber. The T241 cells were treated with the MetAP-2 inhibitor TNP-470 (final concentration 2 µM) for one hour in the incubator chamber. Following incubation, the cells were washed by repeated centrifugation to pellet cells and re-dissolve in PBS. After this step, the cells were pooled into a PBS buffer. This mix of cells was then subjected to FACS sorting using a MoFlo XDP from Beckman Coulter. Cells were either sorted by their GFP fluorescence (T241) or by the lack of fluorescence (K562). The sorted cells were then aliquoted in 8 tube PCR strips and subjected to heating to temperatures ranging from 44 to 52° C. with two degree increments. After heating, the cells were snap frozen in $N_2$ (I) and freeze thawed. The resulting cell debris together with precipitated protein was pelleted by centrifugation at 20000*g for 20 minutes. The supernatants, containing various amount of the target protein (MetAP-2) were subjected to standard SDS-Page and Western blot analysis using a specific primary MetAP-2 antibody (Santa Cruz Biotechnology SC-365637) at 1:400 dilution in non-fat dietary milk.

Lysate of the cells were prepared by harvest of cells and suspending cell-pellet in Phosphate-buffered saline (PBS) to a cell concentration of 100000 cells/ml, freeze-thawed three cycles in $N_2$ (I) and the lysed cells were cleared from cell debris by centrifugation. The cleared lysate was divided in three equal parts, and supplemented with DNA oligos PG1 or PG2 dissolved in ultrapure water, and as a control an equal amount of water was added to the third aliquote.

Following incubation for 30 minutes at room temperature, the three samples were aliquoted to 8 tube PCR strips and heated to increasing temperatures (36 to 57° C. with three degree increments) for duration of three minutes. After heating the samples were cooled and precipitated protein was separated by centrifugation at 20000*g for 17 minutes. The remaining supernatants, containing various amounts of soluble protein was subjected to standard SDS-Page and Western blot analysis using a specific primary p53 antibody (Santa Cruz Biotechnology SC-126) at 1:400 dilution in non-fat dietary milk. The resulting protein bands on the Western blot membranes were integrated and plotted.

Equal numbers of cells ($0.5$-$1.0 \times 10^6$ cells per data point) were seeded in T-25 cell culture flasks (BD Biosciences, San Jose, Calif., USA) or 12-well cell culture plates (Corning Inc., Corning, N.Y., USA) in appropriate volume of culture medium and exposed to a drug for 3 hours in an incubator chamber (with 5% $CO_2$) (Memmert GmbH, Schwabach, Germany). Control cells were incubated with an equal volume of diluent for the corresponding drug. Following the incubation the cells were harvested (either directly or detached from the surface using Trypsin/EDTA solution (Sigma-Aldrich)) and washed with PBS in order to remove excess drug. Equal amounts of cell suspension were aliquoted into 0.2 mL PCR microtubes, and excess PBS was removed by centrifugation to leave 10 uL or less PBS in each microtube. These cell pellets were used for the thermal shift assay.

For transport inhibitions experiments equal numbers of K562 cells ($0.6 \times 10^6$ cells per data point) were seeded in 12-well cell culture plates in appropriate volume of culture medium and pre-incubated with a transport inhibitor (suramin or NBMPR) for 30 min in an incubator chamber. The appropriate inhibitor concentrations were determined in preliminary thermal shift assay experiments (data not shown). Control cells were incubated with an equal volume of DMSO. The cells were then exposed to varying concentrations of an appropriate drug (methotrexate or 5-FU, respectively) for 3 hours in an incubator chamber. Following the incubation the drug-containing media were removed by centrifugation; the cells were harvested, washed with PBS and prepared for CETSA as described above.

For time-course experiments equal numbers of K562 cells ($0.6 \times 10^6$ cells per data point) were seeded in T-25 cell culture flasks and exposed to varying concentrations of raltitrexed. Cell culture aliquots were removed at specified times; the cells were washed with PBS and prepared for the thermal shift assay as described above.

For re-feeding experiments equal numbers of K562 cells ($0.6 \times 10^6$ cells per data point) were seeded in 12-well cell culture plates in appropriate volume of culture medium and exposed to varying concentrations of raltitrexed for 10 min., 30 min., or 3 hours in an incubator chamber. Following the incubation the drug-containing media were removed by centrifugation; the cells were harvested, washed with PBS and prepared for the thermal shift assay as described above. The removed media were used to resuspend freshly pelleted non-treated K562 cells ($0.6 \times 10^6$ cells per data point). These cell suspensions were transferred to fresh 12-well cell culture plates and incubated for additional 3 hours. The cells were harvested, washed and prepared for thermal shift assay as described above.

Figure 3:
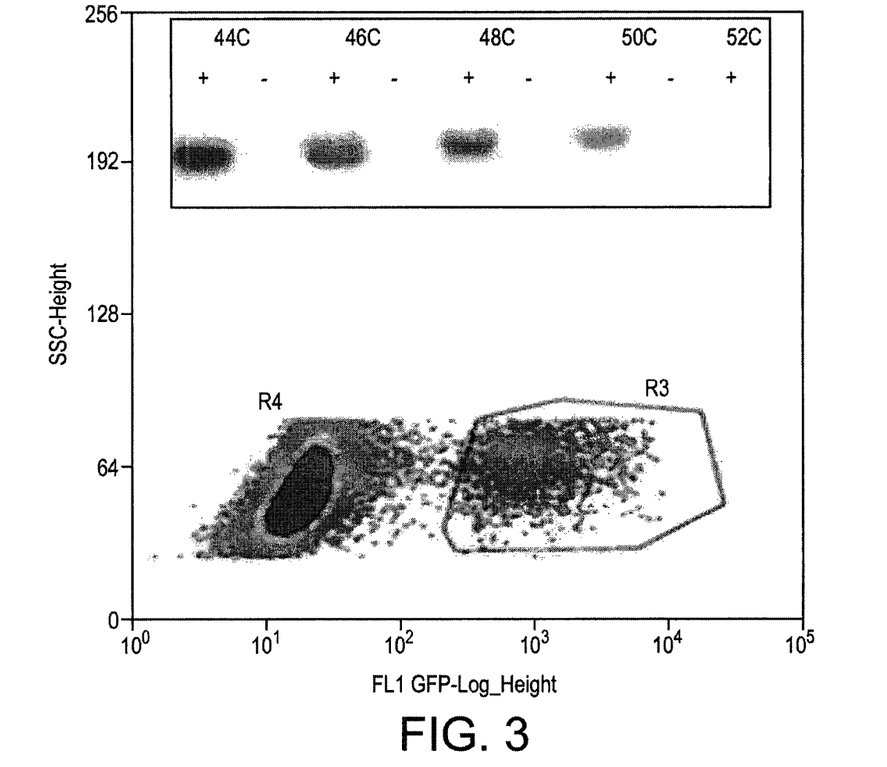
FIG. 3—a) A feasibility of cell resolved thermal shift assay samples composed of fibroblasts and lymphocytes where only lymphocytes were treated with the anti-angiogenic drug TNP-470 as reported by the stabilisation the target protein Methionine aminopeptidase-2 (inlay figure, a dark band shows presence of heat stabilised protein).

Results can be seen in FIG. 3.

EXAMPLE 5

The overall aim of this experiment is to predict drug response from proteome wide CETSA profiles of acute myeloid leukemia (AML) cells from patient samples. These profiles reflect the specific activation of cellular processes such as metabolism, cell signaling, signal transduction and transport processes in the specific patient sample, process where some are likely to also change when drugs are added.

Reference proteome wide CETSA data sets are measured for patient cohorts responding significantly better to one of two type of therapeutic AML regimes, specifically the 1) 7+3 and 2) FLAG-IDA therapies. 5 patients were used in each reference sample. Measurements were done from samples before therapy was initiated, where one sample was measured without drug added and one sample where measured where drug was added for 4 hours ex vivo. The subsequent response history of the patients after testing both therapies led to their assignment to one of the two reference groups. The measured CETSA reference profiles gave characteristics for the responders of the two therapies 1) and 2). Subsequently CETSA measurements were made for 7 patients (A-G) to provide additional support for which initial therapy would be appropriated for these patients.

To establish correlations between patient pairs, patient 1 and patient 2, differences between the melting curves of corresponding proteins in the two patient samples was determined as the differences for the measurement of remain soluble protein F (X-axis in typical melting curves) for all temperature points (Y-axis in typical melting curves), see formula 1. Melting curves to be used for the correlation measurements were selected using a similar strategy as in Savitski et al, were proteins with flat melting curves and high variance were excluded. Initial temperatures were scaled to 1.0. The difference of the melting curves for all proteins were summed and divided by the number of proteins to give an average difference, the R-factor, between the CETSA measurement for patient 1 and 2. Typically more than 3000 proteins, overlapping in two patient data sets, were used for comparison of patient pairs. The correlation of the samples within each of the two reference groups using therapies 1) and 2) respectively, are better than any cross correlation between the two groups (table 1).

$$R\text{-factor} = \sum_{Temp=1,10} \sum_{N=1-Nproteins}(\text{Abs}(FP1_{Temp,N} - FP2_{Temp,N}))_{Temp,N}/N \quad \text{Formula 1}$$

Where $FP1(2)_{Temp,N}$ is remaining soluble protein at temperature Temp for patient 1(or 2), Nproteins are the number of overlapping proteins used in the comparison Out of the 7 non-reference patient samples 5 correlate significantly better (have lower R-factors) to one of the two groups, while 2 have a similar correlation to group 1) and 2). The 5 correlation samples then give indications for that the therapy should be selected as for the reference groups, i.e. Patient A,C,F should try 1) 7+3 therapy while patient B and G should try 2) FLAG-IDA therapy. The progress of the response could subsequently be followed by taking samples after 1-2 days of treatment to correlate with CETSA response for the reference groups after 1-2 days (not done in the present experiment).

by 3 min incubation at 20° C. The cells were subsequently lysed using three freeze-thaw cycles and solubilized in buffer. The samples were then centrifuged at 90,000 g for 25 min at 4° C. The soluble fractions were isolated and subsequently used for MS analysis.

MS-experiment: 10-plex TMT (TMT10, Thermo-Fisher) was used for isobaric labeling of peptides to allow 10 temperatures in each patient sample to be measured in each experiment. MS experiments were done similarly as in Savitski et. In short, prefractionation of samples before injection into the to a Q Exactive (Thermo Scientific) was done using high pH reversed-phase chromatography The samples were subsequently injected into an Ultimate3000 nanoRLSC (Dionex) with a 50 cm×100 µM reversed-phase columns (Reprosil). Protein identification and quantification was done using Mascot 2.4 and Proteome Discoverer.

The invention claimed is:
1. A method for identifying a biomarker indicative of a reduced response to a drug in a patient comprising the steps of:

TABLE 1

R-factor correlations between different patient CETSA data sets. Above diagonal, non-drug treated samples and below diagonal, drug treated samples. PN, K where N is patient number and K is the type of therapy. PA to PG are patients with known responses.

|  | P1, 1 | P2, 1 | P3, 1 | P4, 1 | P5, 1 | P1, 2 | P2, 2 | P3, 2 | P4, 2 | P5, 2 | PA | PB | PC | PD | PE | PF | PG |
|---|---|---|---|---|---|---|---|---|---|---|---|---|---|---|---|---|---|
| P1, 1 | 1.0 | 1.71 | 2.43 | 1.92 | 1.86 | 2.94 | 4.34 | 5.15 | 3.72 | 3.74 | 2.32 | 3.92 | 2.32 | 5.79 | 4.12 | 1.92 | 5.62 |
| P2, 1 | 2.31 | 1.0 | 2.73 | 1.94 | 2.36 | 3.73 | 3.42 | 4.37 | 3.75 | 3.75 | 1.91 | 3.19 | 2.38 | 4.63 | 5.73 | 2.43 | 4.33 |
| P3, 1 | 2.51 | 2.50 | 1.0 | 1.99 | 2.10 | 4.47 | 5.78 | 3.72 | 5.78 | 3.72 | 1.79 | 4.63 | 1.91 | 3.72 | 4.31 | 1.73 | 3.68 |
| P4, 1 | 2.71 | 2.82 | 1.91 | 1.0 | 1.91 | 3.76 | 4.76 | 4.58 | 4.76 | 4.23 | 2.41 | 3.43 | 1.99 | 3.34 | 4.26 | 1.77 | 2.97 |
| P5, 1 | 2.51 | 1.81 | 1.92 | 2.71 | 1.0 | 2.42 | 3.58 | 3.53 | 3.77 | 3.54 | 2.91 | 2.63 | 2.51 | 4.29 | 3.64 | 1.75 | 3.64 |
| P1, 2 | 3.63 | 2.74 | 2.91 | 3.51 | 4.10 | 1.0 | 1.99 | 2.40 | 2.10 | 2.34 | 3.43 | 2.62 | 2.32 | 4.78 | 4.26 | 2.62 | 1.77 |
| P2, 2 | 2.75 | 3.73 | 3.71 | 3.33 | 3.43 | 1.73 | 1.0 | 1.30 | 1.88 | 1.54 | 2.93 | 2.65 | 4.74 | 5.38 | 3.54 | 3.76 | 1.76 |
| P3, 2 | 3.14 | 3.12 | 4.85 | 2.74 | 3.75 | 2.16 | 2.20 | 1.0 | 1.54 | 1.91 | 4.63 | 2.33 | 5.52 | 4.27 | 4.53 | 3.67 | 2.77 |
| P4, 2 | 2.73 | 3.88 | 3.71 | 3.57 | 3.76 | 2.28 | 2.41 | 1.77 | 1.0 | 1.74 | 3.93 | 2.48 | 4.78 | 4.75 | 5.32 | 4.38 | 2.13 |
| P5, 2 | 3.96 | 3.42 | 3.71 | 4.22 | 4.72 | 1.92 | 1.91 | 1.67 | 1.71 | 1.0 | 4.87 | 1.96 | 4.54 | 3.82 | 4.42 | 3.96 | 1.74 |
| PA | 1.71 | 2.56 | 2.33 | 1.97 | 1.75 | 2.63 | 2.92 | 3.61 | 2.47 | 3.37 | 1.0 |  |  |  |  |  |  |
| PB | 3.23 | 3.93 | 3.53 | 2.63 | 2.93 | 1.91 | 1.83 | 2.42 | 1.99 | 1.86 |  | 1.0 |  |  |  |  |  |
| PC | 1.95 | 1.99 | 2.73 | 2.51 | 1.94 | 2.61 | 3.31 | 3.14 | 2.95 | 3.53 |  |  | 1.0 |  |  |  |  |
| PD | 3.97 | 4.95 | 3.72 | 3.63 | 4.99 | 4.86 | 3.34 | 2.21 | 4.17 | 3.14 |  |  |  | 1.0 |  |  |  |
| PE | 3.93 | 4.47 | 2.23 | 4.88 | 3.97 | 4.39 | 5.93 | 3.92 | 4.37 | 3.87 |  |  |  |  | 1.0 |  |  |
| PF | 2.7 | 1.91 | 2.51 | 2.53 | 2.35 | 3.63 | 3.63 | 3.63 | 3.63 | 3.63 |  |  |  |  |  | 1.0 |  |
| PG | 2.93 | 5.13 | 3.55 | 4.33 | 5.63 | 2.73 | 3.20 | 2.91 | 2.44 | 2.91 |  |  |  |  |  |  | 1.0 |

Material and Methods

Patient AML cells: Peripheral blood or bone marrow aspirate were used to collect cells from patient AML blasts, after obtaining patient informed consent. Mononuclear cells were isolated with Ficoll-Paque Plus (Amersham Biosciences). Samples from 5 reference patients with better response to 1) 7+3 therapy was selected and 5 reference patients with better response to 2) FLAG-IDA therapy. 7 patients where response was not know was also selected.

CETSA experiment: Cells from each patient were divided in two samples which were processed in parallel. On sample was incubated for 4 hours at 37° C. with a therapeutic drug combination to simulate the initial therapeutic drug exposure, while the other sample was incubated 4 hours with vehicle (the buffer for the therapeutic drug combination). CETSA experiments were done similarly as in Martinez Molina et al. In short, cells were allocated for the CETSA experiments and 10 aliquots from each patient sample corresponding to melting curves (37° C. to 67° C., 3° C. steps). Samples were heated in parallel in a PCR machine for 3 min to the respective temperature, followed a) obtaining heated sample aliquots
   by heating either i) a sample from a patient having a reduced response to the drug or ii) a sample from a patient responsive to the drug to a series of different temperatures and removing an aliquot after heating to each temperature, wherein in i) and ii) said patient or said sample has been treated with said drug; or
   by dividing either i) a sample from a patient having a reduced response to the drug or ii) a sample from a patient responsive to the drug into several aliquots and heating each aliquot to a different temperature within a series of temperatures, wherein in i) and ii) said patient or said sample has been treated with said drug;
b) separating soluble from insoluble protein in each heated sample aliquot of i) or ii); and
c) analysing by mass spectrometry either or both the soluble and insoluble fractions of step b) to determine the amount of at least one protein therein and either comparing with the amount of said at least one protein in a corresponding fraction obtained from heated and separated sample aliquots from a patient responsive to the drug when i) is heated and separated in steps a) and b), or comparing with the amount of said at least one protein in a corresponding fraction obtained from heated and separated sample aliquots from a patient having a reduced response to the drug when ii) is heated and separated in steps a) and b), to identify at least one protein which has a different melting temperature in the sample from the reduced drug response patient, compared to the sample from drug responsive patient, wherein both samples undergo the heating and separation steps using temperatures that differ by at most 2° C., and wherein the biomarker is not the target protein to which the drug binds to treat the patient's condition.

2. The method of claim 1 wherein step c) determines the melting temperature of one or more proteins.

3. The method of claim 1 wherein said sample is a tissue sample.

4. The method of claim 3 wherein said tissue sample is blood, serum, plasma, lymph, cerebrospinal fluid, mucus, urine, faces or is a liquid or solid tumour sample.

5. The method of claim 1 wherein said sample from a patient responsive to the drug and said sample from a patient having a reduced response to the drug are of the same type.

6. The method of claim 1 wherein said sample from a patient responsive to the drug and said sample from a patient with a reduced response to the drug are taken from the same patient at different times.

7. The method of claim 1 wherein said sample comprises a plurality of cell types and a step of cell sorting is carried out before said analysis step.

8. The method of claim 1 wherein said sample comprises cells and said method further comprising a cell lysis step before step b).

9. The method of claim 8 wherein said lysis step is carried out after step a).

10. The method of claim 1 wherein said separation step is carried out by filtration, centrifugation or affinity capture of soluble protein.

11. A method for identifying a biomarker indicative of a reduced response to a drug in a patient comprising the steps of a) obtaining heated sample aliquots
  by heating a sample from a patient responsive to the drug to a series of different temperatures and removing an aliquot after heating to each temperature, wherein said patient or said sample has been treated with said drug, or
  by dividing a sample from a patient responsive to the drug into several aliquots and heating each aliquot to a different temperature within a series of temperatures, wherein said patient or said sample has been treated with said drug;

b) separating soluble from insoluble protein in each heated sample aliquot of step a), c) analysing by mass spectrometry either or both the soluble and insoluble protein fractions of step b) to determine the amount of at least one protein therein, d) repeating steps a) to c) with a sample from a patient having a reduced response to the drug wherein said patient or sample has been treated with said drug, and e) identifying at least one protein which has a different melting temperature in the sample from the drug responsive patient compared to the sample from the reduced drug responsive patient, wherein said protein is a biomarker indicative of a reduced response to the drug, wherein both samples undergo the heating and separation steps using temperatures that differ by at most 2° C., wherein the biomarker is not the target protein to which the drug binds to treat the patient's condition, and wherein step d) is optionally carried out prior to or simultaneously to steps a) to c).

12. A method for generating a proteome profile from a sample, indicative of a reduced response to a drug in a patient comprising the steps of:

a) obtaining heated sample aliquots
  by heating a sample from a patient responsive to the drug to a series of different temperatures and removing an aliquot after heating to each temperature, wherein said patient or sample has been treated with said drug, or
  by dividing a sample from a patient responsive to the drug into several aliquots and heating each aliquot to a different temperature within a series of temperatures, wherein said patient or said sample has been treated with said drug, b) separating soluble from insoluble protein in each heated sample aliquot of step a), c) analysing by mass spectrometry either or both the soluble and insoluble protein fractions of step b) to determine the melting temperature of a plurality of proteins, d) repeating steps a) to c) with a sample from a patient having a reduced response to the drug, wherein said patient or sample has been treated with said drug, and e) producing a proteome profile for the plurality of proteins indicating quantitative differences between the melting temperatures obtained for proteins from the sample from a patient responsive to the drug and the melting temperatures obtained for proteins from the sample from a patient with a reduced response to the drug, wherein said proteins comprise proteins which are not the target protein to which the drug binds to treat the patient's condition, and f) identifying as a biomarker of a reduced response to the drug at least one protein which has a different melting temperature in the sample from the patient responsive to the drug compared to the sample from the patient having a reduced response to the drug, wherein said at least one protein is not the target protein to which the drug binds to treat the patient's condition, wherein both samples undergo the heating and separation steps using temperatures that differ by at most 2° C., and wherein optionally step d) may be performed prior to or simultaneously to steps a) to c).

* * * * *